(12) United States Patent
Orinski (10) Patent No.: US 10,441,778 B2
(45) Date of Patent: Oct. 15, 2019

(54) OPTICAL STIMULATION IMPLANT

(71) Applicant: Boston Scientific Neuromodulation Corporation, Valencia, CA (US)

(72) Inventor: William G. Orinski, Reno, NV (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 103 days.

(21) Appl. No.: 15/470,767

(22) Filed: Mar. 27, 2017

(65) Prior Publication Data

US 2017/0281928 A1    Oct. 5, 2017

Related U.S. Application Data

(60) Provisional application No. 62/314,817, filed on Mar. 29, 2016.

(51) Int. Cl.
| | | |
|---|---|---|
| *A61N 1/36* | (2006.01) | |
| *A61N 1/372* | (2006.01) | |
| *A61N 1/05* | (2006.01) | |
| *A61B 5/00* | (2006.01) | |

(52) U.S. Cl.
CPC ............ *A61N 1/0534* (2013.01); *A61B 5/686* (2013.01); *A61N 1/0536* (2013.01); *A61N 1/0539* (2013.01); *A61N 1/3605* (2013.01); *A61N 1/36082* (2013.01); *A61N 1/37211* (2013.01); *A61N 1/0526* (2013.01); *A61N 1/0529* (2013.01)

(58) Field of Classification Search
CPC .. A61N 5/0601; A61N 5/0603; A61N 5/0622; A61N 1/0534; A61N 1/0539; A61N 1/36064; A61N 1/36067; A61N 1/36075; A61N 1/36082; A61N 1/36092; A61N 1/36096; A61N 1/36103
See application file for complete search history.

(56) References Cited

U.S. PATENT DOCUMENTS

| | | | |
|---|---|---|---|
| 5,445,608 A * | 8/1995 | Chen | A61N 5/0601 604/19 |
| 6,304,784 B1 | 10/2001 | Allee et al. | |
| 6,427,086 B1 * | 7/2002 | Fischell | A61B 5/0476 607/45 |
| 6,921,413 B2 | 7/2005 | Mahadevan-Jansen et al. | |

(Continued)

OTHER PUBLICATIONS

Chung, Hoon, et al., "The Nuts and Bolts of Low-Level Laser (Light) Therapy," Ann Biomed Eng., 40(2), Feb. 2012, pp. 516-533.

(Continued)

*Primary Examiner* — George R Evanisko
(74) *Attorney, Agent, or Firm* — Lewis & Reese, PLLC (57) ABSTRACT

An implantable medical device for providing phototherapy to a patient's brain is disclosed. The device includes a housing containing a light source for providing phototherapy to a patient. A light path is attached to the housing. The implantable medical device is configured to be positioned between a patient's skull and scalp with the light path extending into the patient's brain, such that light from the light source can irradiate a target position within the patient's brain. The implantable medical device is powered and controlled by an implantable pulse generator (IPG) that may be implanted into a patient's tissue remotely from the device and connected to the device by wire leads.

11 Claims, 6 Drawing Sheets

(56) References Cited

U.S. PATENT DOCUMENTS

| | | | |
|---|---|---|---|
| 7,395,118 B2 | 7/2008 | Erickson | |
| 8,761,889 B2 | 6/2014 | Wingeier et al. | |
| 8,936,630 B2 | 1/2015 | Denison et al. | |
| 9,042,988 B2* | 5/2015 | DiLorenzo | A61N 1/36053 607/45 |
| 9,521,955 B2* | 12/2016 | Ma | A61B 5/0084 |
| 2007/0213783 A1* | 9/2007 | Pless | A61N 1/36071 607/42 |
| 2009/0054955 A1* | 2/2009 | Kopell | A61N 5/0601 607/88 |
| 2009/0088680 A1 | 4/2009 | Aravanis et al. | |
| 2012/0259393 A1 | 10/2012 | Benabid et al. | |
| 2012/0296444 A1* | 11/2012 | Greenberg | A61B 5/4064 623/25 |
| 2013/0184794 A1 | 7/2013 | Feldman et al. | |
| 2013/0317575 A1 | 11/2013 | Deisseroth et al. | |
| 2014/0094674 A1* | 4/2014 | Nurmikko | A61B 5/04001 600/378 |
| 2016/0367809 A1* | 12/2016 | Patel | A61N 1/36064 |
| 2018/0154152 A1* | 6/2018 | Chabrol | A61N 1/36067 |
| 2018/0369608 A1* | 12/2018 | Chabrol | A61N 5/0601 |

OTHER PUBLICATIONS

Darlot, Fannie, et al., "Near-Infrared Light is Neuroprotective in a Monkey Model of Parkinson's Disease," Annuals of Neurology, 79(1), Jan. 2016, pp. 59-75.

Desmet, Kristina, et al., "Near-infrared Light as a Possible Treatment Option for Parkinson's Disease and Laser Eye Injury," Proc SPIE—The International Society for Optical Engineering, vol. 7165, 2009, pp. 716503-716510.

* cited by examiner

OPTICAL STIMULATION IMPLANT

CROSS REFERENCE TO RELATED APPLICATIONS

This is a non-provisional application of U.S. Provisional Patent Application Ser. No. 62/314,817, filed Mar. 29, 2016, which is incorporated by reference in its entirety, and to which priority is claimed.

FIELD OF THE INVENTION

The present application relates to implantable devices, and more specifically, to a medical device for providing phototherapy to a patient's brain.

INTRODUCTION

Implantable stimulation devices deliver electrical stimuli to nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and Deep Brain Stimulators (DBS) to treat motor and psychological disorders, and other neural stimulators to treat urinary incontinence, sleep apnea, shoulder subluxation, etc. The description that follows will generally focus on the use of the invention within a Deep Brain Stimulation (DBS) system. However, the present invention may find applicability with any Implantable Pulse Generator (IPG) or in any IPG system.

Figure 1:
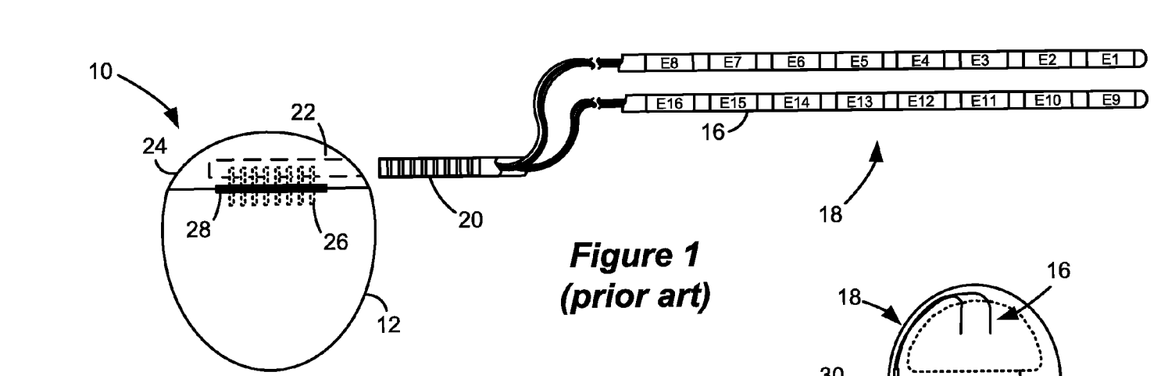
FIG. 1 shows an Implantable Pulse Generator such as a Deep Brain Stimulator (DBS), in accordance with the prior art.

As shown in FIG. 1, a DBS system includes an Implantable Pulse Generator (IPG) 10, which includes a biocompatible device case 12 comprising titanium for example. The case 12 typically holds circuitry and a battery (not shown), which battery may be either rechargeable or primary in nature. The IPG 10 is coupled to electrodes 16 via one or more electrode leads 18 (two of which are shown). The proximal ends of the leads 18 include electrode terminals 20 that are coupled to the IPG 10 at one or more connector blocks 22 fixed in a header 24, which can comprise an epoxy for example. Contacts in the connector blocks 22 contacts the electrode terminals 20, and communicate with the circuitry inside the case 12 via feedthrough pins 26 passing through a hermetic feedthrough 28 to allow such circuitry to provide stimulation to or monitor the various electrodes 16.

Figure 2:
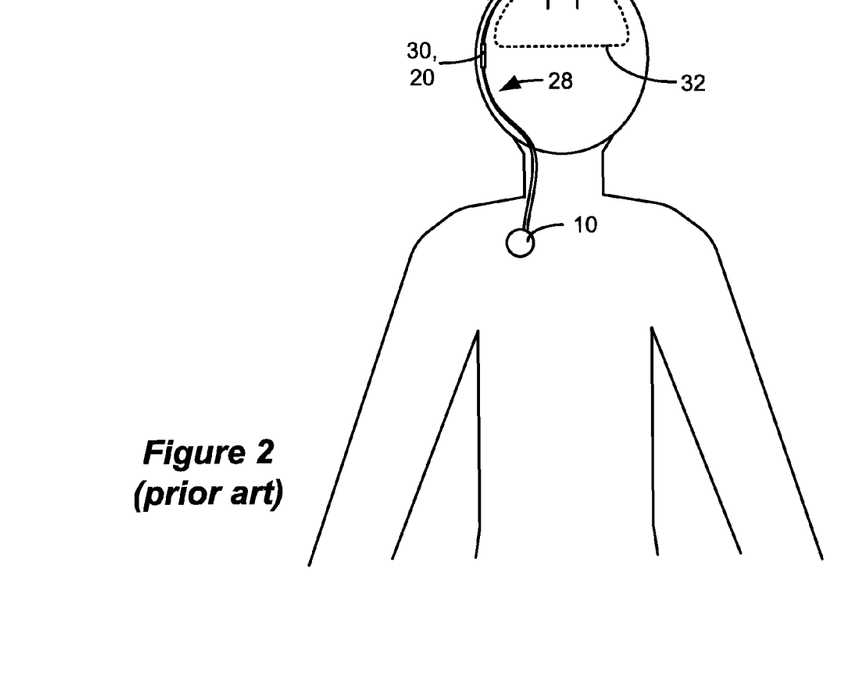
FIG. 2 shows the IPG of FIG. 1 as implanted in a patient, in accordance with the prior art.

In a DBS application, as is useful in the treatment of Parkinson's disease for example, the IPG 10 is typically implanted under the patient's clavicle (collarbone), and the leads 18 with electrodes 16 are implanted through holes drilled in the skull in the left and right and side of the patient's brain 32, as shown in FIG. 2. Specifically, the electrodes 16 may be implanted in the subthalamic nucleus (STN), the pedunculopontine nucleus (PPN), the Global Pallidus Interna (GPI), and/or the Ventral Intermediate Nucleus (VIM). In this regard, four leads 18 may be necessary for full coverage, as discussed further in U.S. Patent Application Publication 2013/0184794. Thereafter, a tunnel is formed under the patient's skin and fascia (e.g., over the skull, behind the patient's ear, down the neck) to connect the proximal ends of the leads 18 to the IPG 10. As the distance from the skull holes to the IPG 10 is rather long, extender leads 28 may be employed having receptacles 30 into which the electrode terminals 20 of the leads 18 can be inserted. The extender leads 28 have their own electrode terminals (not shown) to allow connection to the connector blocks 22 in the IPG 10.

While DBS therapy employed in the manner shown can provide symptomatic relief for a patient, it does not slow the underlying progression of the disease. Thus, treatment methodologies that not only provide symptomatic relief, but that also stop or slow the underlying neurological degeneration, are needed. Phototherapy, i.e., irradiating neurons with light, is one such treatment. For example, animal studies have shown that irradiating neurons with near-infrared (NIr) light can curtail degenerative processes within the neurons. See, e.g., Darlot, et al., Near-Infrared Light is Neuroprotective in a monkey model of Parkinson's disease, *Ann Neurol*, 2016, 79(1), 59-75; and Desmet, et al., Near-infrared Light as a Possible Treatment Option for Parkinson's Disease and Laser Eye Injury, 2009, *Proc SPIE-The International Society for Optical Engineering*, 716503-10. Thus, there is a need for medical devices for delivering phototherapy to neurons within a patient's brain.

DETAILED DESCRIPTION

Figure 3:
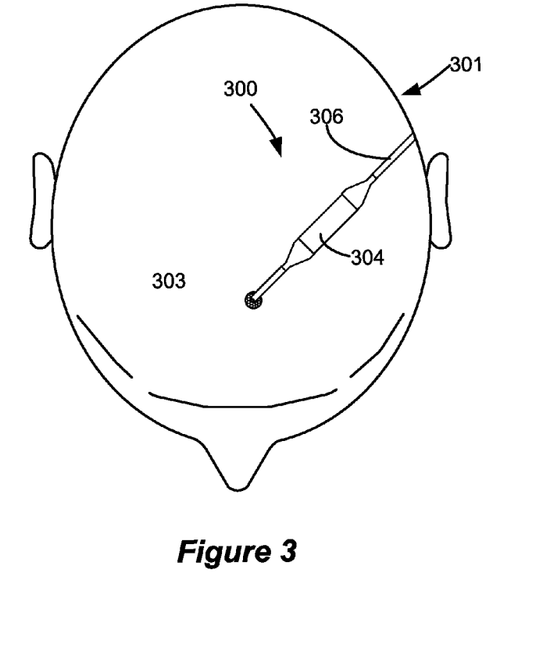
FIG. 3 shows an optical implant (OI) for providing phototherapy to a region of a patient's brain.
Figure 4:
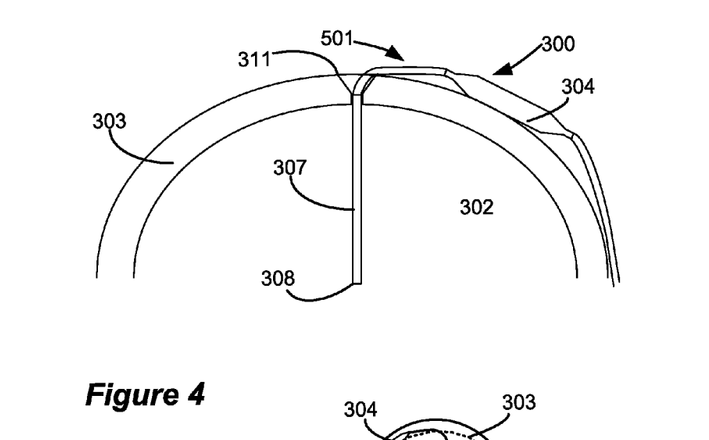
FIG. 4 shows a different view of the OI of FIG. 3.
Figure 5:
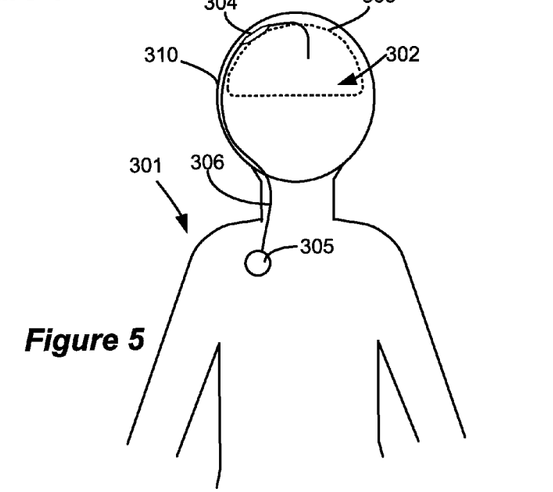
FIG. 5 shows a patient equipped with an OI connected to an IPG.

FIGS. 3, 4, and 5 show an optical implant (OI) 300 for providing phototherapy to the brain 302 of a patient 301. OI 300 includes an implant housing 304 that is mounted to a patient's skull 303 and is connected to an implantable pulse generator (IPG) 305 by a power lead 306 whereby the OI 300 receives power and programming data from the IPG 305. The implant housing 304 and the power lead 306 are typically placed between the patient's skull 303 and scalp 310. The IPG 305 is typically implanted inferior to the patient's clavicle in the pectoral region or in some other fleshy region.

As shown in FIG. 3, viewing the top of a patient's head, the implant housing 304 is designed to lie generally flat against the patient's skull and underneath the scalp, and preferably above the patient's ear proximate to the temporal or parietal bones. Such placement is preferable because the skull in these locations is generally flat, therefore allowing the implant housing 304 to lay relatively flat. However, because the implant housing 304 is flexible at certain locations, perfect flatness of the skull is not required. The implant housing 304 is generally about 8-10 mm in thickness, thin enough to be comfortably positioned between the patient's scalp and skull.

The implant housing 304 includes a light source and supporting electronics for the light source, both of which are discussed in more detail below. The implant housing 304 attaches to a light path 501, which provides a path for therapeutic light to a target area of the patient's brain. The light path 501 includes a light pipe 307, configured to extend into the patient's brain. The light pipe 307 may include a diffuser (or lens) 308 for focusing or diffusing the light within a target area of the patient's brain.

When implanting the OI, the physician drills a hole 311 in the patient's skull inserts the distal end of the light pipe 307 into an appropriate location in the patient's brain 302. The hole 311 may be conical in shape, that is, it may be wider at the superficial surface of the skull and narrower at the deep surface. The physician can secure the properly placed light pipe 307 using standard means, such as by cementing or plugging. Thereafter, the implant housing 304 can be secured to the skull. For example, the implant housing 304 may include one or more screw holes (or partial holes), as known in the art, to allow the implant housing 304 to be firmly secured to the skull with bone screws once it is correctly positioned.

Figures 6, 7:
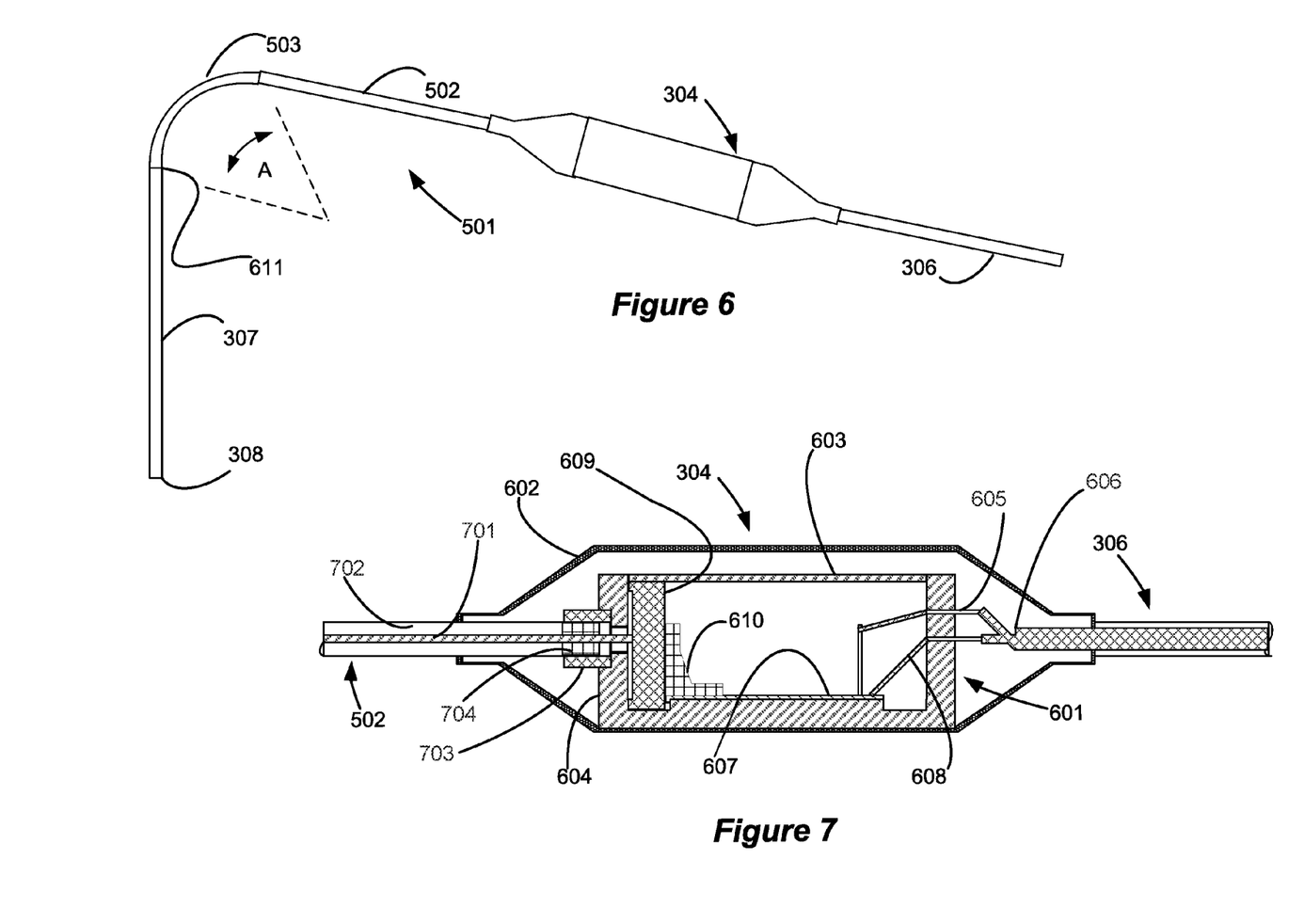
FIG. 6 shows an OI.
FIG. 7 shows a cross-section cutaway view of an OI.

FIGS. 6 and 7 illustrate the implant housing 304 and related assemblies in greater detail. As illustrated in FIG. 6, the implant housing 304 is configured between the power lead 306 and a light delivery section 501. The light delivery section comprises a proximal section 502, an arcuate section 503, and the light pipe 307.

FIG. 7 shows a cutaway view of the implant housing 304. The implant housing comprises a hermetically sealed compartment 601 that is covered in an overmolding material such as silicone 602. The overmolding material may also cover a portion of the power lead 306. The overmolding serves to integrate the implant housing 304 and the power lead 306 and also to provide soft surfaces for portions of the implant housing 304 that might come into contact with a patient's tissue/fascia. The hermetically sealed compartment 601 comprises a top cover 603, which covers an inner housing 604. According to some embodiments the top cover 603 and inner housing 604 are made of titanium. The inner housing 604 includes feedthroughs 605, whereby conducting wires 606 of the power lead 306 makes electrical contact with a printed circuit board (PCB) 607 contained within the inner housing 604. Contact wires 608 connect feedthroughs 605 with the PCB 607.

A light source 609 can be connected to the PCB 607. The light source 609 may be held in place by a mounting bracket 610. The PCB 607 may be electrically grounded to the inner housing 604 by a grounding pin (not shown).

According to certain embodiments, the light source 609 is a light emitting diode (LED) or a laser diode. A physician may choose a light source 609 to provide a particular wavelength of light that the physician believes will be therapeutic. For example, the light wavelength be in the in the near-UV spectrum (~300-400 nm), the visible spectrum (~390-750 nm), or the near-IR spectrum (~750-1400 nm). Particular examples of light sources emit in a narrow band centered at about 670 nm or at about 740 nm. An example of a suitable light source the Ushio HL6748MG, (Ushio OPTO Semiconductors, Inc.), which is a 670 nm/10 mW AlGaInP laser diode.

The light source 609 may be mounted to the PCB 607, which includes electronics for driving the light source 609.

The PCB 607 may include additional electronics for operating and controlling the OI. For example, the PCB 607 may be connected to a temperature sensor. Such a temperature sensor may be configured to monitor the temperature of the inner housing 604 and to interrupt power to the light source 609 if the temperature exceeds a certain value.

The housing 304 is connected to a light delivery section 501, which comprises a proximal section 502, an arcuate section 503, and a light pipe 307. The light delivery section is configured to deliver light from the light source 609 to a region of a patient's brain. In the embodiment illustrated in FIG. 7, the light delivery section comprises an optical fiber 701 sheathed within a cladding material 702. The light delivery section 501 may include additional sheathing materials (not shown) to provide reinforcement, as is known in the art. For ease of discussion, the combination of the optical fiber 701 and any sheathing layers 702 are referred to as the optical conduit. The optical conduit couples light from the light source 609 for delivery. The optical conduit penetrates through an orifice in the inner housing 604 to couple with the light source 609. One or more coupling optical components may be disposed between the optical conduit and the light source 609, but are not shown in the illustration. The optical conduit is held in place, for example, by a fiber ferrule mounting bracket 703 that secures a fiber ferrule 704.

Referring again to FIG. 6, arcuate section 503 provides a bend radius having an angle A that is large enough that no significant loss of light occurs at the bend. Generally, the bend should have a radius of 30 mm or more, though more acute bends can be achieved with specialized fiber optic materials. As shown in FIG. 4, the conical shape of the hole 311 in the patient's skull 303 facilitates achieving an adequate bend radius.

According to some embodiments, the optical fiber 701 extends the entire length of the light delivery section 501. In other words, the optical fiber 701 extends from the inner housing 604, through the proximal section 502, the arcuate section 503, and the light pipe 307 and may terminate at the diffuser 308. Alternatively, the optical fiber 701 may terminate within the light delivery section 501. For example, the optical fiber 701 may terminate at the distal end 611 of the arcuate section 503. According to that embodiment, the light pipe 307 may simply comprise a hollow tube that provides a conduit for the light from the optical fiber 701 to the diffuser 308. The light pipe may be made of a material such as a metal, for example, titanium. According to some embodiments, the light pipe 307 may be detachable from the arcuate section 503, allowing the physician to swap out light pipes of different lengths. For example, the light pipe may snap or screw into the arcuate section.

Figure 8:
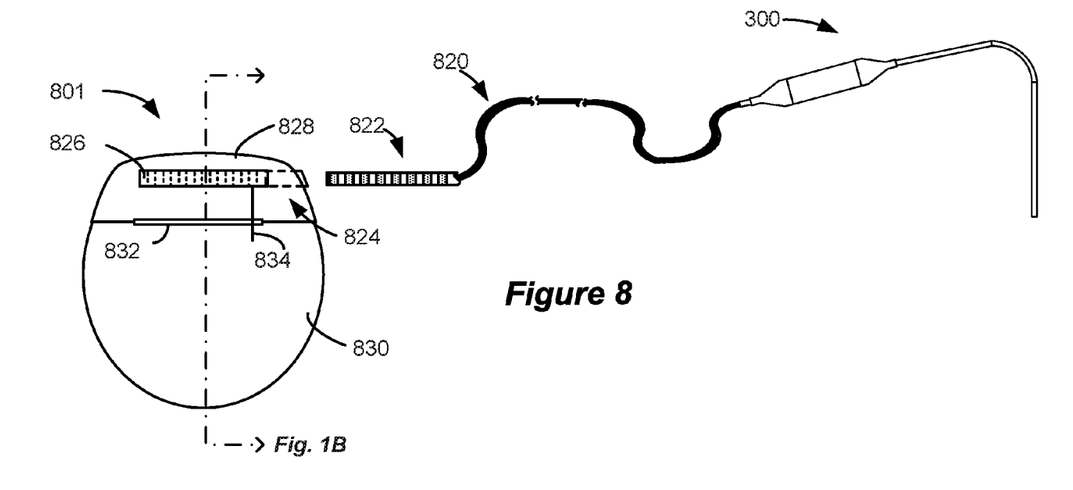
FIG. 8 shows an OI attached to an IPG.

FIG. 8 illustrates an IPG 801 for powering and controlling the OI 300. Implantable Pulse Generator (IPG) 801 shown in plan and cross-sectional views in FIGS. 8 and 9, respectively. The IPG 801 includes a biocompatible device case 830 that holds the circuitry and battery 836 (FIG. 9) necessary for the IPG to function. The IPG 801 is coupled to the OI 300 via lead wires 820. The lead wires 820 are also coupled to proximal contacts 822, which are insertable into lead connector 824 fixed in and encompassed by a header 828 on the IPG 801, which header can comprise an epoxy for example. Once inserted, the proximal contacts 822 connect to header contacts 826 in the lead connector 824, which is in turn coupled by electrode feedthrough pin 834 through an electrode feedthrough 832 to circuitry within the case 830 (connection not shown). Case 830 can be formed of case portions 830a and 830b (FIG. 9) which are laser welded together and to the electrode feedthrough 832.

In the illustrated IPG 801, there are eight proximal contacts 822, with the header 828 containing a single lead connector 824 to receive the lead's proximal end. However, the number of leads and contacts in an IPG is application specific and therefore can vary. For example, some therapeutic applications may involve using traditional stimulating electrodes in conjunction with phototherapy. In such an application, the IPG 801 may include additional lead connectors for receiving the electrodes. In the illustrated IPG 801, the eight proximal contacts and corresponding leads may transmit power (positive and ground wires), data, and commands between the IPG 801 and the OI 300. Depending on the amount and type of data and commands, the number of leads and contacts may differ.

Figure 9:
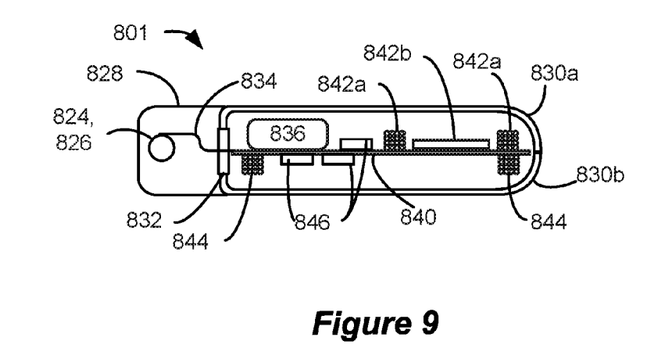
FIG. 9 shows an IPG for powering and controlling OI.

As shown in the cross section of FIG. 9, the IPG 801 includes a printed circuit board (PCB) 840. Electrically coupled to the PCB 840 are the battery 836, which in this example is rechargeable; other circuitry 846 coupled to top and/or bottom surfaces of the PCB, including a microcontroller and other circuitry necessary for IPG operation; a telemetry antenna—842a and/or 842b—for wirelessly communicating with an external device; a charging coil 844 for wirelessly receiving a magnetic charging field from an external charger for recharging the battery 836; and the electrode feedthrough pins 834 (connection to circuitry not shown). If battery 836 is permanent and not rechargeable, charging coil 844 would be unnecessary.

Both of telemetry antennas 842a and 842b can be used to transcutaneously communicate data through the patient's tissue to an external device, but are different in shape and in the electromagnetic fields they employ. Telemetry antenna 842a comprises a coil, which can bi-directionally communicate with an external device via a magnetic induction communication link, which comprises a magnetic field of typically less than 10 MHz operable in its near-field to communicate at a distance of 12 inches or less for example. Circuitry 846 includes telemetry circuitry coupled to the coil antenna 842a, including driver circuitry for energizing the coil antenna 842a to transmit data and receiver circuitry for resolving data received at the coil 842a. Such telemetry circuitry also operates in accordance with a modulation scheme (defining how data to be transmitted is modulated, and will be demodulated when received) and a communication protocol (defining the manner in which the data is formatted). A typical modulation scheme used for magnetic induction communications via coil antenna 842a is Frequency Shift Keying (FSK), although other modulation schemes could also be used.

Telemetry antenna 842b comprises a short-range Radio-Frequency (RF) antenna that operates in accordance with a short-range RF communication standard and its underlying modulation scheme and protocol to bi-directionally communicate with an external device along a short-range RF communication link. Short-range RF communication link typically operates using far-field electromagnetic waves ranging from 10 MHz to 10 GHz or so, and allows communications between devices at distances of about 50 feet or less. Short-range RF standards operable with antenna 42b include, for example, Bluetooth, BLE, NFC, Zigbee, WiFi (802.11x), and the Medical Implant Communication Service or the Medical Device Radiocommunications Service (both collectively referred to herein as "MICS" for short). Short-range RF antenna 842b can take any number of well-known forms for an electromagnetic antenna, such as patches, slots, wires, etc., and can operate as a dipole or a monopole. Circuitry 846 would include telemetry circuitry coupled to the short-range RF antenna 842b, again including driver and receiver circuitry.

IPG 801 could contain both the coil antenna 842a and the short-range RF antenna 842b to broaden the types of external devices with which the IPG 801 can communicate, although IPG 801 may also include only one of antenna 842a and 842b.

Examples of external devices operable to communicate with the IPG 801 include external devices used to adjust the therapy the OI 300 will provide to the patient. The therapy may require pulsing the light source to provide light pulses having a particular duration, pulse width, recovery time, etc. For example, the IPG 801 may be programmed to cause the light source to be on for 5-10 seconds and off for a minute. That cycle may be repeated continually for a number of hours, days, or indefinitely. Upon evaluation, the physician may decide to reprogram the IPG 801 to deliver a different pattern of therapy and may use an external device to communicate with the IPG 801 to implement that change.

According to some embodiments, phototherapy can be combined with electrical neuromodulation. For example, the patient may be fitted with one or more DBS electrode leads 18 (FIGS. 1 and 2) in addition to an OI 300. In such an instance, the IPG 801 is configured to control both the electro-active electrode leads and the OI 300.

Figures 10, 11:
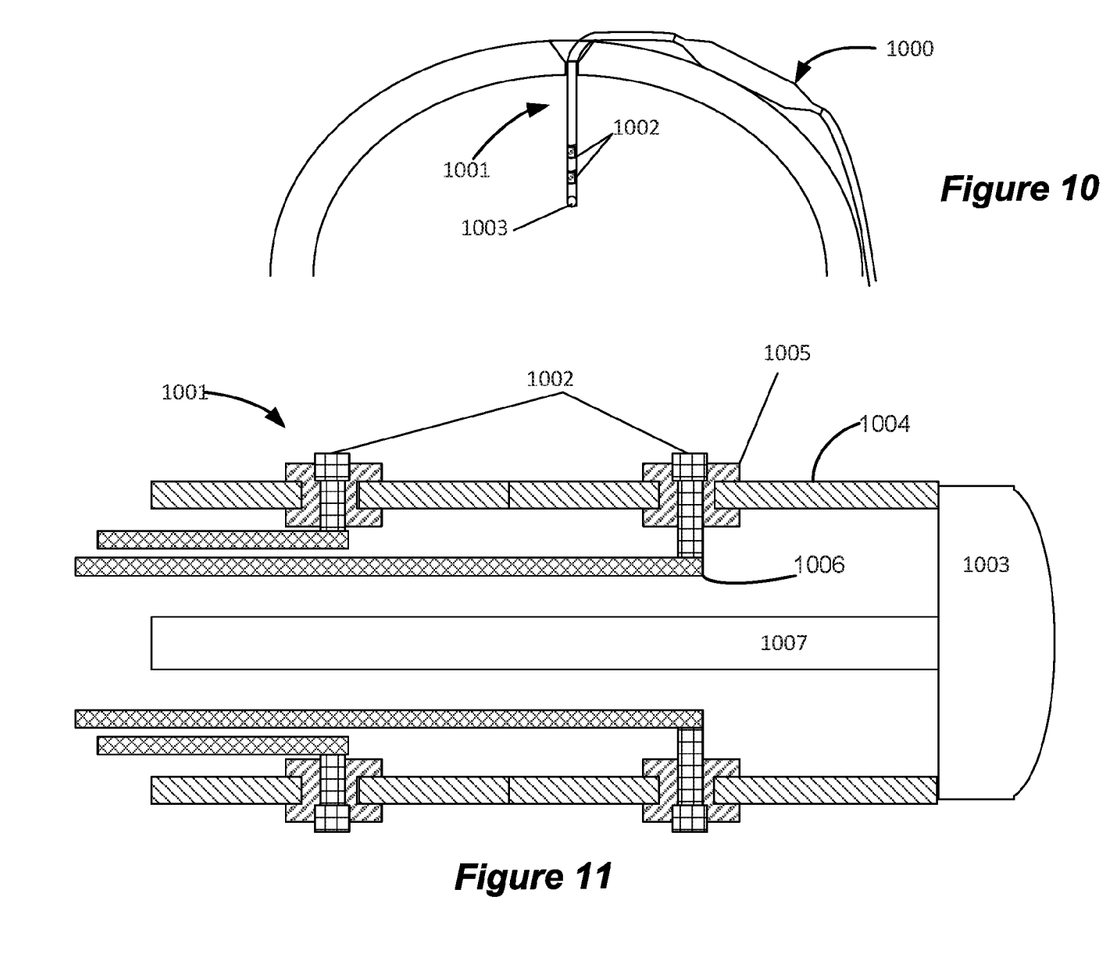
FIG. 10 shows an OI configured to provide phototherapy and electrical neuromodulation.
FIG. 11 shows a light pipe for an OI that includes electrodes for providing electrical neuromodulation.

According to other embodiments, the OI 300 can be configured to provide both phototherapy and electrical neuromodulation. FIGS. 10 and 11 illustrate an OI 1000 that includes a light pipe 1001 configured with electrodes 1002 and a diffuser 1003. The electrodes 1002 may be ring electrodes, for example, and may be insulated from the body 1004 of the light pipe 1001 by insulators 1005. The electrodes can be connected to the IPG 801 by lead wires 1006. The light pipe 1001 illustrated in FIG. 11 includes a light guide 1007, such as an optical fiber. As described above, the light pipe may simply be a tube having a diffuser.

Figure 12:
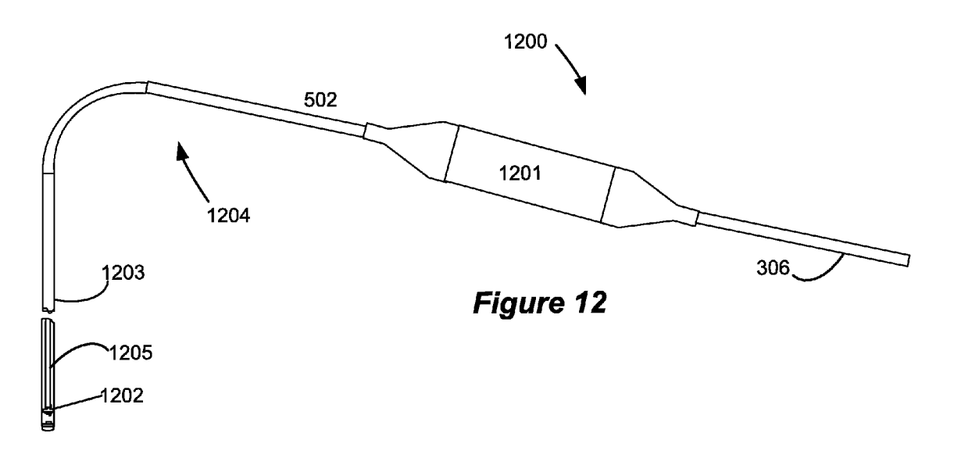
FIG. 12 shows an OI configured with a light source contained within an optical lead.
Figure 13:
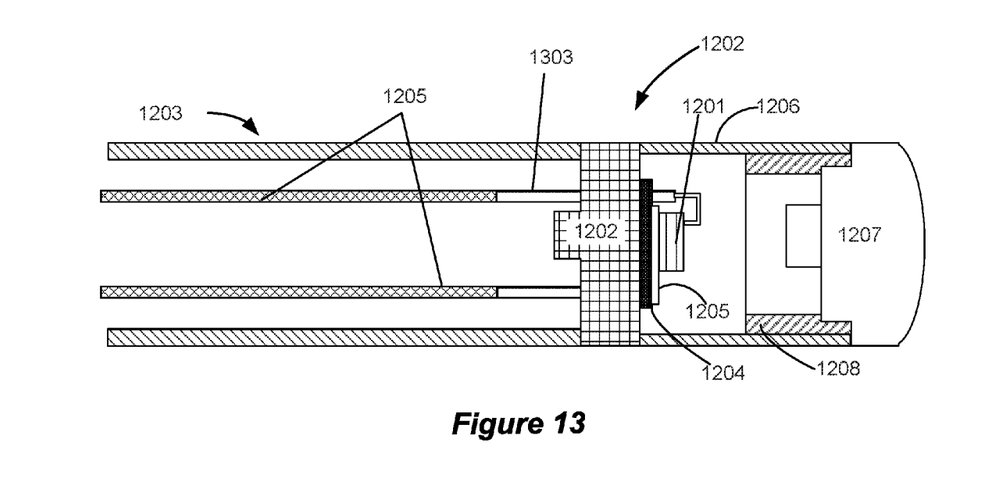
FIG. 13 shows a light source contained within an optical lead.

FIGS. 12 and 13 illustrate an alternative embodiment of an OI 1200. Instead of being contained within an implant housing 1201, the light source 1202 is configured within an optical lead 1203, which replaces the light pipes illustrated in the earlier OIs. The optical lead 1203 may attach to the light delivery section 1204 similarly to the attachment of the light pipe to the light delivery sections described above, except that optical communication is not required. Instead, only electrical communication is required. Electrical conductors 1205 running within the optical lead 1203 transmit power and/or signals from the implant housing 1201 to the light source 1202. Configuring all or part of the light source within an optical lead 1203 makes it possible to reduce the size of the OI and the implant housing 1201.

Power and signals from the IPG are communicated to the implant housing 1201 by a power lead 306. Within the implant housing the power and signals may be communicated to a PCB or other substrate via one or more feedthroughs and conductors, as described above. According to some embodiments, the PCB or other substrate may include circuitry for driving/controlling the light source 1202. According to other embodiments, the PCB or other substrate may simply include conductors and/or feedthroughs for providing electrical contact with the conductors 1205 within the optical lead 1203.

FIG. 13 illustrates the light source 1202 in greater detail. The light source may include an LED 1201, such as an EPGAP 660 nm LED. The LED 1201 may be mounted to a two-pin feedthrough 1202 configured with pins 1303. The conductors 1205 connect to the pins 1303, which provide electrical power and signals to the LED 1201. The feedthrough 1202 may be a ceramic material, such as Kryoflex, for example. One or more connector plates may be used to mount the LED 1201 to the feedthrough 1202. In the illustrated embodiment, the mounting arrangement includes an insulating plate 1204 and a connecting plate 1205. The insulating plate 1604 may comprise a polymeric material, such as Kapton, for example.

The light source 1202 may further include a housing tube 1206 and an optical element 1207, such as a sapphire optical diffuser or lens. The housing tube 1206 may be titanium, for example. The optical element 1207 may be connected to the housing tube 1206 via a fitting 1208. The fitting 1208 may be a ceramic seal, such as Kryoflex, for example.

It should be appreciated that the embodiments having a light source contained within an optical lead can also be configured to include electrical stimulation, similarly to the embodiments illustrated in FIGS. 10 and 11. In such embodiments, the optical lead includes electrodes, such as ring electrodes and may contain additional conductors for communicating the electrical stimulation signals.

While the invention herein disclosed has been described by means of specific embodiments and applications thereof, numerous modifications and variations could be made thereto by those skilled in the art without departing from the scope of the invention set forth in the claims.

What is claimed is:

1. A medical device, comprising:
    a housing configured to be mounted between a patient's skull and scalp and to receive electrical power via one or more electrical leads from an implantable pulse generator (IPG) implanted in the patient remote from the patient's head;
    a light source contained within the housing configured to be powered by the electrical power received from the IPG; and
    a light path attached to and extending from the housing and configured to provide a path for light from the light source to a target neural area, wherein the light path comprises:
        a proximal section configured to traverse a portion of the patient's skull between the skull and scalp,
        an arcuate section configured to penetrate through a hole in the skull, and
        a light pipe configured to penetrate the brain to the target neural area, the light pipe comprising a hollow tubular member having a first end and a second end, wherein the second end comprises a diffuser or lens attached to the hollow tubular member, wherein,
        a first end of the proximal section connects to the housing and a second end of the proximal section connects to a first end of the arcuate section, and wherein
        a second end of the arcuate section connects to the first end of the light pipe, and
        a fiber optic member contained within the proximal section and the arcuate section and terminating in the arcuate section so that the fiber optic member does not extend through the tubular member of the light pipe and configured to allow light from the fiber optic member to traverse the interior of the hollow tubular member to the diffuser or lens.

2. The medical device of claim 1, wherein the housing comprises a hermetically sealed inner portion overmolded in an overmolding material.

3. The medical device of claim 2, wherein the overmolding material is a silicone.

4. The medical device of claim 2, further comprising one or more feedthroughs providing electrical communication for the one or more electrical leads into and out of the hermetically sealed inner portion.

5. The medical device of claim 2, wherein the hermetically sealed inner portion contains a printed circuit board (PCB) electrically connected to the light source.

6. The medical device of claim 5, further comprising a temperature sensor electrically connected to the PCB.

7. The medical device of claim 1, wherein the light pipe second end contains the diffuser.

8. The medial device of claim 1, wherein the light pipe is configured to connect to and disconnect from the arcuate section.

9. The medical device of claim 8, wherein the light pipe is configured to connect to and disconnect from the arcuate section by screwing or snapping to/from the arcuate section.

10. The medical device of claim 1, wherein the light pipe further comprises at least one electrode configured to provide electrical neuromodulation.

11. The medical device of claim 10, wherein the at least one electrode comprises a ring electrode integrated with the light pipe.

* * * * *